United States Patent [19]

Van Lysel

[11] Patent Number: 5,170,421

[45] Date of Patent: Dec. 8, 1992

[54] CONTROLLED OPTIMIZATION OF RELATIVE EXPOSURE LEVELS IN DUAL ENERGY DSA

[75] Inventor: Michael S. Van Lysel, Madison, Wis.

[73] Assignee: Wisconsin Alumni Research Foundation, Madison, Wis.

[21] Appl. No.: 800,500

[22] Filed: Nov. 29, 1991

[51] Int. Cl.⁵ .............................................. H05G 1/64
[52] U.S. Cl. ....................................... 378/99; 358/111
[58] Field of Search ......................... 358/111; 378/99

[56] References Cited

U.S. PATENT DOCUMENTS 4,442,537 4/1984 Haendle ................................. 378/99

Primary Examiner—Craig E. Church
Attorney, Agent, or Firm—Andrus, Sceales, Starke & Sawall

[57] ABSTRACT

A method for obtaining high quality images in dual energy digital subtraction angiography (DSA) with reduced signal to noise ratio (SNR) while simultaneously reducing patient X-ray exposure utilizes a larger aperture for the low-energy beam to obtain a lower patient exposure and a smaller aperture for the high-energy X-ray beam to obtain a decrease in image noise.

3 Claims, 3 Drawing Sheets

CONTROLLED OPTIMIZATION OF RELATIVE EXPOSURE LEVELS IN DUAL ENERGY DSA

BACKGROUND OF THE INVENTION

The present invention relates to a method of performing digital subtraction angiography (DSA) and more specifically to a method of performing dual energy digital subtraction angiography.

In the past, temporal or time subtraction has been utilized to enhance images obtained in digital subtraction angiography performed with low-energy X-ray beams. However, this method is plagued by misregistration artifacts due to patient motion.

This problem was overcome by the use of dual energy digital subtraction angiography which utilized both a low-energy X-ray beam and a high-energy X-ray beam. However, the signal to noise ratio (SNR) of dual energy DSA is substantially lower than that of the temporal subtraction DSA method due to the weighted subtraction and the high noise level associated with the high-energy image.

It is an object of the present invention to provide a method of performing dual energy DSA which optimizes the signal to noise ratio with respect to patient X-ray exposure.

SUMMARY OF THE INVENTION

A method of performing dual energy DSA which optimizes the signal to noise ratio with respect to the patient X-ray exposure.

In accordance with one aspect of the invention, a dual aperture is provided which provides a larger aperture for the low-energy X-ray beam in order to reduce the patient exposure to the low-energy X-ray beam (for conventional single-aperture dual-energy DSA, patient exposure is dominated by the low-energy beam).

In accordance with another aspect of the invention, the dual aperture provides a smaller aperture for the high-energy X-ray beam to minimize the noise associated with the high-energy beam.

In accordance with yet another aspect of the invention, the signal-to-noise ratio is optimized with respect to patient exposure when the aperture for the low-energy beam has an area approximately five times greater than that for the high-energy beam.

The present invention thus provides a method for optimizing the signal to noise ratio in a dual energy DSA image while at the same time optimizing the patient exposure.

BRIEF DESCRIPTION OF THE DRAWINGS

The drawings illustrate the best method currently contemplated for carrying out the invention.

In the drawings.

DETAILED DESCRIPTION OF THE INVENTION

Figure 1:
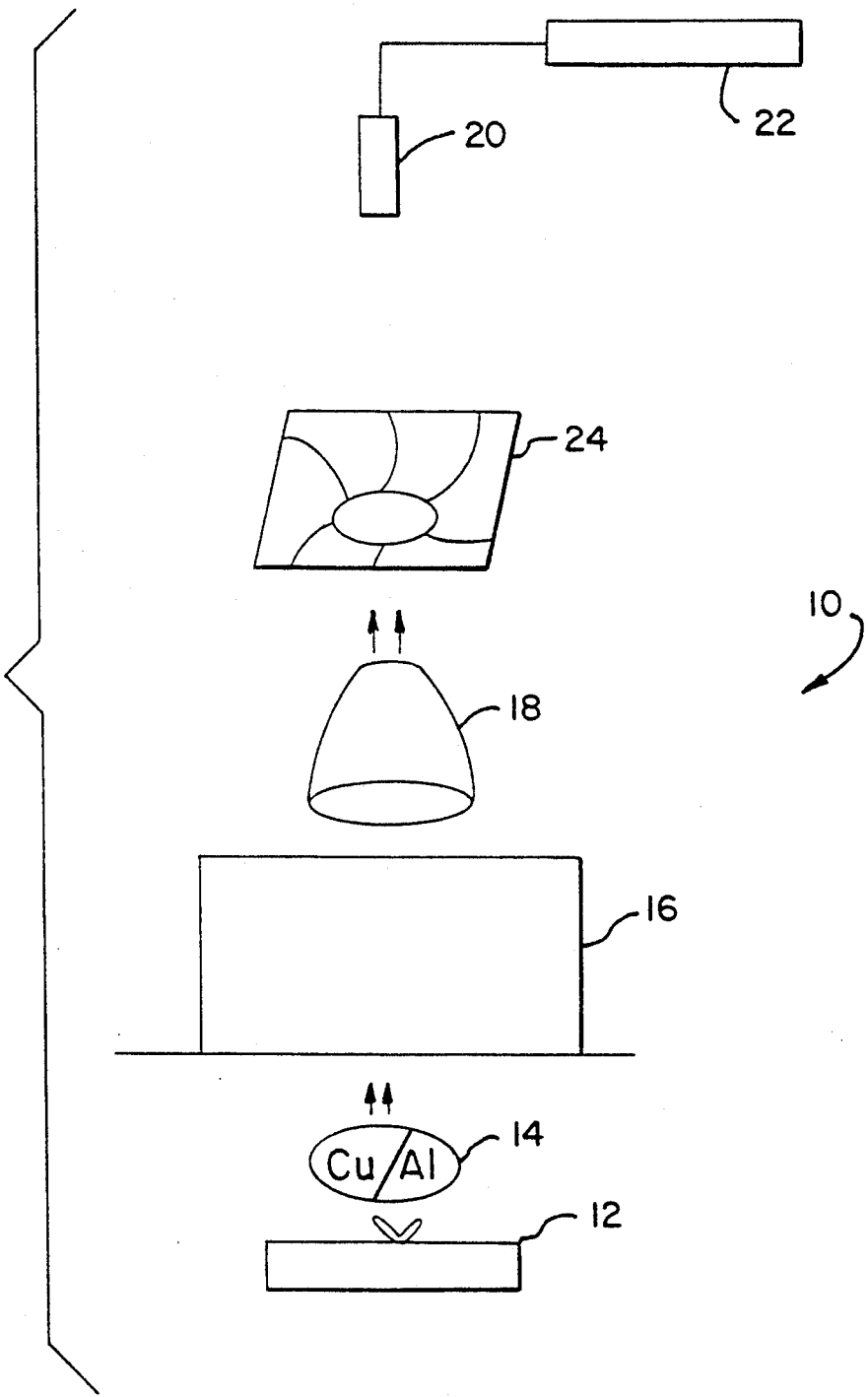
FIG. 1 is a schematic of a dual energy digital subtraction angiography system adapted to perform the method of the present invention.

FIG. 1 schematically illustrates a dual energy digital subtraction angiography system 10 adapted to perform the method of the present invention.

The system includes an X-ray generator and tube 12 capable of generating dual energy X-ray beams. In the experiments utilizing this procedure, a Philips Optimus M200 X-ray generator was utilized. X-ray generator 12 provided a low-energy beam of 65 kVp and a high-energy beam of 120 kVp. A filter wheel 14 was utilized to provide 2.5 millimeters of aluminum filtration for the low-energy beam and 2.5 millimeters of aluminum plus 2.16 millimeters of copper filtration for the high-energy beam. A 20 centimeter block of lucite 16 was utilized as a phantom patient and a standard image intensifier 18 was utilized to provide a light image for a Philips XTV6 video camera 20. The video image was enhanced by a standard image processor/computer 22.

In order to perform the method of the present invention, system 10 is further provided with adjustable aperture 24 located between the image intensifier and the video camera.

Utilizing a system such as that shown in FIG. 1, a series of images were acquired at different aperture areas for both the low-energy and high-energy beams. The mAs required to produce a constant video signal was recorded. The video aperture had previously been calibrated so that the relationship between (i) the image intensifier entrance exposure and (ii) the video aperture area required to produce a given video signal amplitude was known. In concordance with Philip's standard for measuring image intensifier entrance exposure, this calibration was performed with a 1.5 mm Cu phantom at 75 kVp without the anti-scatter grid. Using this relationship, video aperture "area" is often given in micro Roentgen/frame. The area of variable aperture 24 varied directly and inversely to the ratio of the image intensifier entrance exposure, i.e. the area of aperture 24 for an exposure of 25 $\mu$R/frame was double the area for an exposure of 50 $\mu$R/frame.

Subtraction images were formed from these images to eliminate brightness non-uniformities. The noise in these images was measured by determining the standard deviation in image values in a small region-of-interest in the center of the images, correcting for the square-root of two increase due to the subtraction process. The noise in a dual-energy image, as a function of the video aperture area, was then determined from the equation $$\sigma_E = \sqrt{(\sigma^2 L + R^2 T \sigma^2 H)}$$

where $\sigma_L$, $\sigma_H$ and $\sigma_E$ are the measured noise, at the aperture setting in question, in the low-, high-, and dual-energy images, respectively and $R_T = 1.3$ is the ratio of the low- and high-energy X-ray attenuation coefficients for tissue.

In addition to the image noise, patient exposure as a function of aperture area was determined for the low- and high-energy beams. This was accomplished by measuring the table-top mR/mAs at 65 kVp (2.5 mm Al) and 120 kVp (2.16 mm Cu+2.5 mm Al) with an MDH model 1015 X-ray ionization chamber. The mR/mAs was then used, in conjunction with the mAs measured during the acquisition of the noise images, to determine the patent exposure as a function of aperture area for the low- and high-energy beams.

Figure 2:
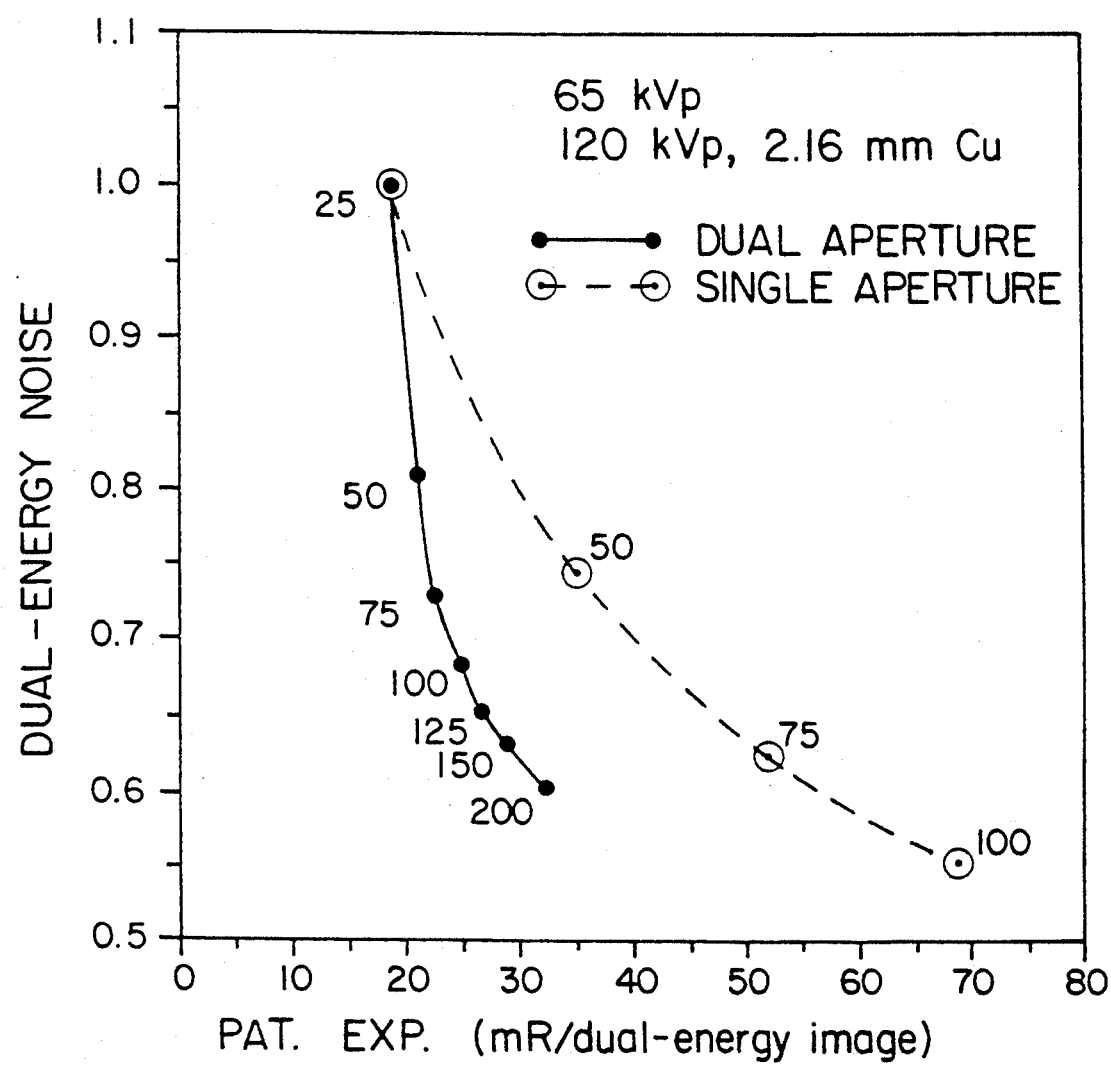
FIG. 2 is a graph plotting the image noise versus patient X-ray exposure.

The resulting plot of the noise in a dual-energy image as a function of patient exposure for both the conventional single-aperture method and the new dual-aperture method is given in FIG. 2. The dual-aperture technique is seen to achieve a given level of image noise at significantly lower patient exposure.

FIG. 2 compares the reduction in image noise for the two techniques versus the required increase in patient exposure. It is seen that the dual-aperture technique has a clear advantage, with the noise dropping rapidly at first with little increase in total patient exposure.

As seen in FIG. 2, a dual-aperture technique, in which the image intensifier exposure is higher for the high-energy beam than the low-energy beam, provides superior signal-to-noise ratio for a given patient exposure in dual-energy DSA. A dual-aperture pair of 25–125 $\mu$R/frame provides the same signal-to-noise ratio as a 70-70 $\mu$R/frame single-aperture pair for 45% less patient exposure.

Figure 3:
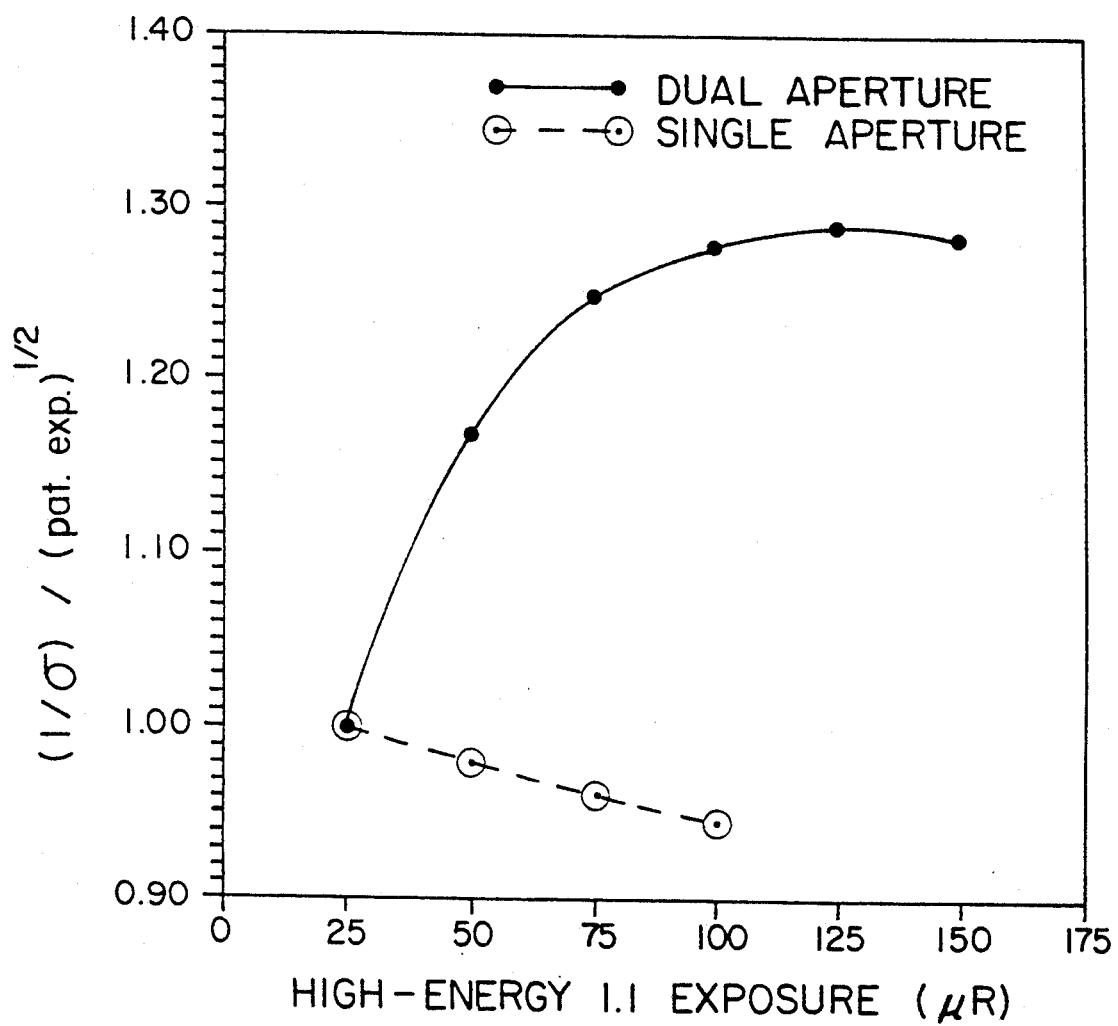
FIG. 3 is a graph showing the efficiency of patient exposure utilization versus various high energy image intensifier exposure levels (i.e. the area of the high-energy video aperture).

The single-aperture technique results in equal image intensifier exposures for both beams. In this case the efficiency of patient X-ray exposure utilization is independent of exposure level, as would be the case for single-energy imaging. The dual-aperture technique fixes the low-energy image intensifier exposure (e.g. at 25 $\mu$R/frame), only the high-energy beam exposure is raised. As seen in FIG. 3, patient exposure is utilized more efficiently in the dual-aperture technique, with a peak in efficiency at a high-energy exposure of approximately 125 $\mu$R/frame (the exact ratio of high-energy to low-energy aperture areas which fully optimize the use of patient exposure will vary depending upon the details of the experimental set-up). The reason for this behavior is that when both energy beams use the same size aperture, dual-energy image noise is dominated by the high-energy image yet the patient exposure from the high-energy beam is only about 15% of that from the low-energy beam.

Various modes of carrying out the invention are contemplated as being within the scope of the following claims particularly pointing out and distinctly claiming the subject matter regarded as the invention.

I claim:

1. A method of optimizing the signal to noise ratio with respect to patient X-ray exposure in a dual energy digital subtraction angiography procedure of the type that utilizes an X-ray generator, an X-ray filter, an image intensifier and a video recording means, said method comprising:

generating a low-energy X-ray beam having a first value of X-ray exposure at the image intensifier, generating a high-energy X-ray beam having a second value of X-ray exposure at the image intensifier, calculating a first ratio of said second value to said first value, providing a variable aperture between the image intensifier and the video recording means, said variable aperture providing a first aperture area for said low-energy beam and a second aperture area for said high-energy beam with the ratio of said first area to said second area substantially equal to said first ratio.

2. The method of claim 1 wherein said aperture ratio is approximately 5:1.

3. The method of claim 1 wherein said low-energy X-ray beam has a value of 25 $\mu$R/frame at the image intensifier and said high-energy beam has a value of 125 $\mu$R/frame at the image intensifier.

* * * * *